United States Patent [19]

Yokota et al.

[11] 3,996,271

[45] Dec. 7, 1976

[54] PROCESS FOR PRODUCING TEREPHTHALIC ACID BY CATALYTIC LIQUID PHASE OXIDATION OF PARA-XYLENE

[75] Inventors: Yoshiro Yokota, Ohtake; Yoshiro Hisatomi, Iwakuni, both of Japan

[73] Assignee: Mitsui Petrochemical Industries, Ltd., Tokyo, Japan

[22] Filed: May 13, 1974

[21] Appl. No.: 469,244

[30] Foreign Application Priority Data

May 15, 1973 Japan .............................. 48-53185

[52] U.S. Cl. .......................... 260/524 R; 260/525
[51] Int. Cl.$^2$ ........................................ C07C 51/33
[58] Field of Search ....................... 260/524 R, 525

[56] References Cited

UNITED STATES PATENTS

| | | | |
|---|---|---|---|
| 2,788,367 | 4/1957 | Bills et al. | 260/525 |
| 2,833,816 | 5/1958 | Safter et al. | 260/524 R |
| 2,838,565 | 6/1958 | Heath et al. | 260/525 |
| 3,082,250 | 3/1963 | Baldwin et al. | 260/524 R |
| 3,452,088 | 6/1969 | Olsen et al. | 260/525 |
| 3,507,913 | 4/1970 | Mato et al. | 260/524 R |
| 3,708,532 | 1/1973 | Ichikawa et al. | 260/525 |

FOREIGN PATENTS OR APPLICATIONS 2,119,762   1972   France

*Primary Examiner*—Anton H. Sutto
*Attorney, Agent, or Firm*—Sherman & Shalloway

[57] ABSTRACT

A process for producing terephthalic acid by the catalytic liquid phase oxidation of para-xylene with either molecular oxygen or a gas containing molecular oxygen and recovering terephthalic acid from the liquid phase oxidation reaction product; characterized in that (1) the recovery of terephthalic acid is performed at a temperature ($T_2$) which satisfies the following equation $$[(T_1 - 150)^{1.9}/150] + 150 \leq T_2 \leq T_1 \leq$$

wherein ($T_1$) is the temperature of the above liquid phase oxidation, and (2) a part or whole of the catalyst-containing mother liquor remaining after the recovery of terephthalic acid is recycled to the catalytic liquid phase oxidation while maintaining it at a temperature ($T_3$) which satisfies the following equation $$T_2 \leq T_3 \leq T_1$$

wherein ($T_2$) is the temperature employed in the recovery of terephthalic acid.

4 Claims, No Drawings

PROCESS FOR PRODUCING TEREPHTHALIC ACID BY CATALYTIC LIQUID PHASE OXIDATION OF PARA-XYLENE

This invention relates to an improved process for producing terephthalic acid having a particle size suitable for separation and recovery from the mother liquor and for drying and an extremely high purity without the need for a purification step.

More specifically, the invention relates to a process for producing terephthalic acid by the catalytic liquid phase oxidation of parxylene with either molecular oxygen or a gas containing molecular oxygen in the presence of acetic acid and a cobalt-containing catalyst at the temperature ($T_1$) of 150° to 250° C. and a pressure of 4 Kg/cm².G to 50 Kg/cm².G and recovering terephthalic acid from the liquid phase oxidation reaction product, characterized in that the recovery of terephthalic acid is performed at a temperature ($T_2$) which satisfies the following equation $$[(T_1 - 150°)^{1.9}/(150°)] + (150°) \leqq T_2 \leqq T_1$$

wherein ($T_1$) is the temperature of the above liquid phase oxidation,
and that a part or whole of the catalyst-containing mother liquor remaining after the recovery of terephthalic acid is recycled to the catalytic liquid phase oxidation while maintaining it at a temperature ($T_3$) which satisfies the following equation $$T_2 \leqq T_3 \leqq T_1$$

wherein ($T_2$) is the temperature employed in the recovery of terephthalic acid.

As a preferred embodiment, the present invention also relates to a process for producing terephthalic acid by the catalytic liquid phase oxidation of para-xylene with either molecular oxygen or a gas-containing molecular oxygen in the presence of acetic acid and a cobalt-containing catalyst at a temperature ($T_1$) of 150° to 250° C. and a pressure of 4 Kg/cm².G to 50 Kg/cm².G, which comprises recovering terephthalic acid from the liquid oxidation reaction product, passing the gaseous oxidation reaction product which contains non-condensable gas, water vapor and acetic acid vapor through a fractionating zone in which the acetic acid vapor is condensed while the water vapor is not condensed, recycling the condensed acetic acid to the oxidation reaction and removing the water vapor, together with the noncondensable gas, from the reaction system; characterized in that the recovery of terephthalic acid is performed at a temperature ($T_2$) which satisfies the following equation $$[(T_1 - 150°)^{1.9}/(150°)] + (150°) \leqq T_2 \leqq T_1$$

wherein ($T_1$) is the tmeperature of the above liquid phase oxidation,
and that a part or whole of the catalyst-containing mother liquor remaining after the recovery of terephthalic acid is recycled to the catalytic liquid phase oxidation while maintaining it at a temperature ($T_3$) which satisfies the following equation $$T_2 \leqq T_3 \leqq T_1$$

wherein $T_2$) is the temperature employed in the recovery of terephthalic acid.

A process for producing terephthalic acid compressing the steps described in the preamble part of the above preferred embodiment is described in French Patent Application No. 7146796 patented on July 10, 1972 as French Patent No. 2,119,762. In this process, the mother liquor resulting from the recovery of terephthalic acid from the reaction product is directly recycled to the oxidation reaction without distillation. The water formed as a by-product of the oxidation reaction which has accumulated in the recycle system (the water may contain a minor amount of acetic acid vapor) is removed out of the system from the gaseous oxidation product at a fractionating zone which is preferably connected directly to the oxidation reaction zone. Accordingly, the operation and apparatus required for the distillation of the mother liquor can be omitted, and the amount of the catalyst can be reduced. Thus, this is a very advantageous continuous process that can be performed on a commercial scale.

It has now been found that in order to maintain the catalytic activity stable and high and provide high purity terephthalic acid with good reproducibility in the performance of the above process, the temperature of recovery of terephthalic acid, that is the filtration temperature for terephthalic acid, has a close relation to the temperature of recycling of the mother liquor. Further investigations of this relation have led to the discovery that the intended improvement can be easily achieved by recovering terephthalic acid at a high temperature of the specific range which is directly related to the temperature ($T_1$) of the liquid phase oxidation reaction, and recycling the mother liquor at this elevated temperature or higher but not higher than the temperature ($T_1$).

The filtering temperature for recycling the mother liquor are considered critical, and by employing these temperatures in the specific ranges, it is possible to maintain the catalytic activity stable and high, and provide terephthalic acid of high purity with good reproducibility in addition to the advantage of the above process of the French Patent that it can be operated on a commercial scale. We have also found that in addition to these improvements over the process of the French Patent, the process of the present invention permits the preparation of terephthalic acid crystals having a particle size suitable for their separation and recovery from the mother liquor with the particle sizes of the crystals being uniform.

Accordingly, an object of this invention is to provide a process for producing terephthalic acid by the catalytic liquid phase oxidation of para-xylene, which can lead to the achievement of the above improvement.

Other objects and advantages of this invention will become more apparent from the following description.

In the catalytic liquid phase oxidation of para-xylene according to the process of this invention, a step of recovering terephthalic acid from the liquid oxidation reaction product is carried out at a temperature ($T_2$) expressed by the following equation $$[(T_1 - 150°)^{1.9}/150°] + 150° \leqq T_2 \leqq T_1$$

wherein $T_1$ is the reaction temperature for the liquid phase oxidaton (condition 1).

The mother liquor from which terephthalic acid has been recovered at such a high temperature is maintained substantially at the above temperature $T_2$. In addition to the above condition 1, it is also necessary in the process of this invention to recycle the mother liquor to the liquid phase oxidation at a temperature ($T_3$) which is maintained within the range from the temperature ($T_2$) to the temperature ($T_1$) for the liquid phase oxidation reaction (condition 2). If either of the conditions 1 and 2 is not satisfied, it is difficult to achieve the above-mentioned improvements.

The oxidation of para-xylene in the present invention can be performed by a known method in a fractionating zone, preferably a catalytic liquid phase oxidation zone to the upper portion of which is directly connected a distillation tower. For example, the oxidation of para-xylene can be performed in the presence of a cobalt-containing catalyst comprising a cobalt compound, a manganese compound and a bromine-yielding compound in an acetic acid solvent at a temperature of 150° to 250° C. and a pressure of 4 to 50 Kg/cm².G using molecular oxygen or a gas containing molecular oxygen such as air. More than half of terephthalic acid is precipitated in the oxidation zone, and the remainder is dissolved in the solvent. The catalyst is always in the state of being activated with oxygen.

Preferably, water formed as a by-product in the catalytic liquid phase oxidation reaction is removed at the fractionating zone provided above the oxidation zone. The connection of an oxidation reaction apparatus forming the oxidation zone to a distillation tower forming the fractionating zone is not limited so long as it has a function of removing the water from the mixture evaporated off from the oxidation reaction apparatus to outside the reaction system, and recycling the condensed acetic acid to the oxidation reaction mixture. Usually, the oxidation reaction apparatus is connected to the distillation tower by a pipe, or the oxidation reaction apparatus is juxtaposed with the distillation tower. It is preferred that water vapor is removed from the fractionating zone to an extent such that the moisture content of the mother liquor is 0.5 to about 10% by weight. A part of the acetic acid may be removed together with the water vapor without causing any trouble. The amount of the acetic acid to be removed at this time is one not hampering the oxidation reaction. In other words, it is such that the ratio of para-xylene to acetic acid in the oxidation reaction apparatus is not markedly changed.

The recovery of terephthalic acid from the liquid oxidation reaction product to be performed at the temperature ($_2$) specified in condition 1 can be carried out by any desired means by which a liquid-solid separation can be effected at the temperature ($T_2$). For example, a filtering device utilizing a liquid cyclone or a centrifugal force is used. Since most of the terephthalic acid separated by filtration at this high temperature is crystallized at the oxidation reaction temperature in the oxidation reaction apparatus, the particle sizes of the crystals are uniform, and the crystals are of high purity without containing particles of finer particle diameters. They can be directly dried to obtain a final product. Alternatively, they can be dried after washing with acetic acid, to obtain a final product.

If the temperature ($T_2$) exceeds the oxidation reaction temperature ($T_1$), there is an inevitable reduction in the activity of the catalyst, and the mother liquor cannot be re-used. Furthermore, if the temperature ($T_2$) is below $[(T_1 - 150°)^{1.9}/150°] + 150°$, terephthalic acid dissolved precipitates together with great quantities of organic impurities, and high purity terephthalic acid cannot be obtained. Accordingly, it is necessary to adjust the temperature ($T_2$) to the above-mentioned range.

In the process of the present invention, the mother liquor remaining after the recovery of terephthalic acid is recycled to the liquid phase oxidation reaction without distillation while maintaining the temperature substantially at the temperature ($T_3$) for the recovery of terephthalic acid. If the mother liquor is recycled after cooling it to a temperature below the temperature ($T_3$), the terephthalic acid is accompanied by organic impurities and precipitates as microcrystals. These microcrystals act as a crystallization nucleus for terephthalic acid formed in the catalytic liquid phase oxidation reaction to make it impossible to maintain the high purity of the resulting terephthalic acid and the good reproducibility of the purity.

In the present invention, all of the mother liquor can be recycled. However, in actual operation, impurities contained in the starting paraxylene or the decomposition product formed in the oxidation reaction apparatus build up, and therefore, it is recommended that some amount of the mother liquor is removed out of the system, and fresh acetic acid is supplied. The amount of the mother liquor to be so removed varies somewhat according to the quality required of terephthalic acid. But it is sufficient that the amount is not more than 10% by weight of the amount of the mother liquor. In view of economic and quality considerations, the preferred amount to be removed is 1 to 5% by weight. The removal of a larger amount of the mother liquor is not economic.

According to the present invention described above in detail, a very simple step of filtering the liquid oxidation reaction product immediately makes it possible to prevent organic impurities such as oxidation intermediates or oxidation by-products from precipitating, and adhering to the terephthalic acid or forming a crystallization nucleus having an abundance of impurities. There is no need at all to use any control device for recovering terephthalic acid of high purity from the reaction product. This can lead to the reduction of the content of organic impurities, especially 4-formylbenzoic acid, contained in the precipitated terephthalic acid to about 100 ppm, and also to the inhibition of precipitating fine particles of terephthalic acid, to enable the production of terephthalic acid crystals of uniform particle sizes having an average particle diameter of about 100 to 160 microns. Therefore, by the present invention, high purity terephthalic acid can be prepared without purification by, for example, recrystallization or oxidation. There is a further advantage that since the particle diameters of the terephthalic acid are uniform and large, it lends itself to easier separability and easier drying.

In addition, the resulting terephthalic acid has very great compatibility with alcohols in esterification, and the mother liquor containing the catalyst can be directly recycled to the oxidation reaction apparatus without using any special device for recovering the catalyst from the mother liquor and recycling it. Thus, in spite of the simplification of the process by omitting the crystallization step and the catalyst recovering step, there can be prepared high purity terephthalic acid of uniform crystal diameters as compared with the process including these two steps also.

When the purity of the product terephthalic acid need not be so high, the oxidation conditions can be made moderate, or the mother liquor containing organic impurities in high concentrations can be recycled directly.

The following examples illustrate the present invention more specifically.

EXAMPLES 1 to 3 and COMPARATIVE EXAMPLES 1 to 4

At the start of oxidation, 100 Kg of para-xylene, 800 Kg of 95% by weight acetic acid, 3 Kg of cobalt acetate, 0.039 Kg of manganese acetate and 2.5 Kg of sodium bromide were fed hourly into an oxidation reactor to which a distillation tower was connected, and air was introduced at a temperature of 200° C. and a pressure of 18 Kg/cm².G to perform the continuous oxidation of para-xylene.

The mixture consisting mainly of acetic acid and water as a by-product which occurred simultaneously with the start of oxidation was distilled at a tower top temperature of 170° C. to remove water from the tower top together with exhaust gases. On the other hand, a greater portion of the acetic acid was recycled, and the water content in the oxidation reactor was maintained constant at 4 to 5% by weight. After a residence time of 53 minutes, the resulting mixture from the oxidation reactor was filtered at the temperatures indicated in Table 1 to separate the terephthalic acid. The terephthalic acid was washed with acetic acid, dried, and recovered. On the other hand, 750 Kg of the mother liquor resulting from the filtration was maintained at the temperatures shown in Table 1, and recycled to the oxidation reactor. At the same time, fresh acetic acid, cobalt acetate, manganese acetate and sodium bromide were continuously supplied at a rate of 70 Kg, 0.15 Kg, 0.002 Kg and 0.6 Kg, respectively, per hour. Under the same conditions as above, the continuous oxidation of para-xylene was performed for the time periods shown in Table 1. The average particle diameter of the resulting terephthalic acid, the content of 4-formylbenzoic acid (4CBA for short) and the molecular absorption coefficient ($\epsilon 380\ m\mu$) of the terephthalic acid are shown in Talbe 1.

EXAMPLE 4

Into the same oxidation reactor as used in Example 1 were fed at the start of oxidation 100 Kg of para-xylene, 1000 Kg of 95% by weight acetic acid, 5.5 Kg of cobalt acetate, 0.054 Kg of manganese acetate and 3.1 Kg of sodium bromide hourly, and air was introduced at a temperature of 185° C. and a pressure of 12 Kg/cm².G to perform the continuous oxidation of para-xylene. The mixture consisting mainly of acetic acid and water as a by-product which occurred simultaneously with the start of oxidation was distilled at a tower top temperature of 160° C. to remove the water from the tower top together with exhaust gases. On the other hand, a greater portion of the acetic acid was recycled. The water content in the oxidation reactor was maintained constant at about 4 to 5% by weight, and after a residence time of 90 minutes, the resulting mixture was filtered to separate terephthalic acid. The terephthalic acid was washed with acetic acid, dried and recovered. On the other hand, 940 Kg of the mother liquor resulting from the filtration was maintained at 160° C. and recycled to the oxidation reactor. Fresh acetic acid, cobalt acetate, manganese acetate and sodium bromide were continuously supplied at a rate of 80 Kg, 0.3 Kg, 0.003 Kg and 0.5 Kg respectively per hour. Under the same conditions as described above, the continuous oxidation of para-xylene was performed for 100 hours. The resulting terephthalic acid had an average particle diameter of 120 $\mu$, a 4-formylbenzoic acid content of 100 ppm and a molecular absorption coefficient ($\epsilon 380\ m\mu$) of 0.009. These results are also given in Table 1.

COMPARATIVE EXAMPLE 5

Example 4 was repeated except that the filtering temperature and the recycling temperature were both changed to 150° C. The resulting terephthalic acid had an average particle diameter of 80 $\mu$, a 4-formylbenzoic acid content of 350 ppm and a molecular absorption coefficient ($\epsilon 380\ m\mu$) of 0.046. These results are also shown in Table 1.

EXAMPLE 5

Into the same oxidation reactor as used in Example 1 were fed at the start of oxidation 100 Kg of para-xylene, 1000 Kg of 95% by weight acetic acid, 0.7 Kg of cobalt acetate, 0.7 Kg of manganese acetate and 1.2 Kg of benzyl bromide hourly. Air was introduced at a temperature of 240° C. and a pressure of 37 Kg/cm².G to perform the continuous oxidation of para-xylene. The mixture consisting mainly of acetic acid and water as a by-product which occurred simultaneously with the start of oxidation was distilled at a tower top temperature of 190° C. to remove the water from the tower top together with exhaust gases. The water content in the oxidation reactor was maintained constant at about 4 to 5% by weight, and after a residence time of 60 minutes, the resulting mixture from the oxidation reactor was filtered at 190° C. to separate terephthalic acid. The terephthalic acid was washed with acetic acid, dried and recovered. On the other hand, 940 Kg of the mother liquor resulting from the filtration was maintained at 190° C., and recycled to the oxidation reactor. Fresh acetic acid, cobalt acetate, manganese acetate and benzyl bromide were supplied at a rate of 80 Kg, 0.035 Kg, 0.035 Kg, and 0.24 Kg respectively per hour. Under the same conditions as above, the continuous oxidation of para-xylene was performed for 100 hours. The resulting terephthalic acid had an average particle diameter of 120 $\mu$, a 4-formylbenzoic acid content of 90 ppm and a molecular absorption coefficient ($\epsilon 380\ m\mu$) of 0.009. These results are also shown in Table 1.

COMPARATIVE EXAMPLE 6

Example 5 was repeated except that both the filtering temperature and the recycling temperature were changed to 170° C. The resulting terephthalic acid had an average particle diameter of 60 $\mu$, a 4-formylbenzoic acid content of 250 ppm, and a molecular absorption coefficient ($\epsilon 380\ m\mu$) of 0.027.

Table 1

| Examples (Ex.) and Comparative Examples (Com.) | Reaction temperature $T_1$ (° C) | $(T_1-150)^{1.9}/150+150$ (° C) | Oxidation time (hours) | Filtering temperature $T_2$ (° C) | Recycling temperature (° C) | Average particle diameter of terephthalic acid ($\mu$) | 4-CBA content (ppm) | Molecular absorption coefficient |
|---|---|---|---|---|---|---|---|---|
| Ex. 1 | -200 | 161 | 100 | 180 | 180 | 150 | 90 | 0.009 |

Table 1-continued

| Examples (Ex.) and Comparative Examples (Com.) | Reaction temperature $T_1$ (° C) | $(T_1-150)^{1.9}/150+150$ (° C) | Oxidation time (hours) | Filtering temperature $T_2$ (° C) | Recycling temperature (° C) | Average particle diameter of terephthalic acid ($\mu$) | 4-CBA content (ppm) | Molecular absorption coefficient |
|---|---|---|---|---|---|---|---|---|
| Ex. 2 | 200 | 161 | 200 | 180 | 180 | 150 | 90 | 0.009 |
| Ex. 3 | 200 | 161 | 100 | 190 | 190 | 150 | 90 | 0.009 |
| Com. 1 | 200 | 161 | 100 | 150 | 150 | 80 | 300 | 0.027 |
| Com. 2 | 200 | 161 | 100 | 150 | 180 | 80 | 300 | 0.032 |
| Com. 3 | 200 | 161 | 200 | 150 | 180 | 80 | 500 | 0.046 |
| Com. 4 | 200 | 161 | 100 | 180 | 110 | 150 | 190 | 0.018 |
| Ex. 4 | 185 | 154 | 100 | 160 | 160 | 120 | 100 | 0.009 |
| Com. 5 | 185 | 154 | 100 | 150 | 150 | 80 | 350 | 0.046 |
| Ex. 5 | 240 | 184 | 100 | 190 | 190 | 120 | 90 | 0.009 |
| Com. 6 | 240 | 184 | 100 | 170 | 170 | 60 | 250 | 0.027 |

What we claim is:

1. In a process for producing terephthalic acid by the catalytic liquid phase oxidation of para-xylene with either molecular oxygen or a gas containing molecular oxygen in the presence of acetic acid and a cobalt-containing catalyst at a temperature $(T_1)$ of 150° to 250° C. and a pressure of 4 to 50 Kg/cm².G and recovering terephthalic acid from the liquid phase oxidation reaction product and directly recycling, without distillation, the catalyst-containing mother liquor remaining after recovery of terephthalic acid to the oxidation reaction zone, the improvement comprising 1. recovering terephthalic acid at a temperature $(T_2)$ which satisfies the following equation $$((T_1 - 150°)^{1.9}/150°) + 150° \leq T_2 \leq T_1$$

wherein $(T_1)$ is the temperature of the above liquid phase oxidation, 2. recycling a part or whole of the catalyst-containing mother liquor remaining after the recovery of terephthalic acid without distillation to the catalytic liquid phase oxidation while maintaining it at a temperature $(T_3)$ which satisfies the following equation $$T_2 \leq T_3 \leq T_1$$

wherein $(T_2)$ is the temperature employed in the recovery of terephthalic acid, and 3. passing the resulting gaseous oxidation reaction product through a fractionating zone in which the acetic acid vapor is condensed while the water vapor is not condensed, recycling the condensed acetic acid to the oxidation reaction zone, and removing the water vapor from the reaction system together with the non-condensable gas.

2. The process of claim 1 wherein the catalyst comprises cobalt, manganese and bromine.

3. The process of claim 1 wherein the amount of the water vapor to be removed is such that the water content of the mother liquor is 0.5 to 10% by weight based on the weight of the mother liquor.

4. The method of claim 1 wherein the terephthalic acid is recovered at the temperature $T_2$ by filtration to thereby recover terephthalic acid crystals of uniform particle size having an average particle diameter of about 100 to 160 microns.

* * * * *

UNITED STATES PATENT AND TRADEMARK OFFICE
CERTIFICATE OF CORRECTION

PATENT NO. : 3,996,271
DATED : December 7, 1976
INVENTOR(S) : YOKOTA, ET AL.

It is certified that error appears in the above-identified patent and that said Letters Patent are hereby corrected as shown below:

Claim 1, column 7, line 31, delete the formula in its entirety and insert the following therefor:

$$-- \frac{(T_1 - 150)^{1.9}}{150} + 150 \leq T_2 \leq T_1 \ --$$

Signed and Sealed this

Twenty-second Day of February 1977

[SEAL]

Attest:

RUTH C. MASON
*Attesting Officer*

C. MARSHALL DANN
*Commissioner of Patents and Trademarks*